United States Patent [19]
Hunds

[11] Patent Number: 5,847,139
[45] Date of Patent: Dec. 8, 1998

[54] PROCESS FOR THE PREPARATION OF 4,6-DIHYDROXYPYRIMIDINE

[75] Inventor: Artur Hunds, Bonn, Germany

[73] Assignee: Huels Aktiengesellschaft, Marl, Germany

[21] Appl. No.: 885,136

[22] Filed: Jun. 30, 1997

[30] Foreign Application Priority Data

Jul. 3, 1996 [DE] Germany ............ 196 26 747.1
Oct. 2, 1996 [DE] Germany ............ 196 40 756.7

[51] Int. Cl.$^6$ ..................... C07D 239/52
[52] U.S. Cl. ............................. 544/319
[58] Field of Search ........................ 544/319

[56] References Cited

FOREIGN PATENT DOCUMENTS 12 00 308   9/1965   Germany .
1 092 144  11/1967   United Kingdom .

OTHER PUBLICATIONS

B.A. Zasonov, et al., Khim. Farm. ZH., vol. 8, No. 12, pp. 28–31, 1974, "Synthesis of 4–(N–Aminobenzolsulphamido)–6–Methoxypyrimidine (Russian)".

D.J. Brown, Journal of Chemical Society, pp. 2312–2314, 1956, "Pyrimidine Reactions. Part I. Pyrimidines from Malondiamide".

Claude Hennart, et al., Bulletin De La Societe Chimique De France, pp. 741 and 742, 1959, "Contribution A La Synthese De La Dichloro–4.6–Pyrimidine".

R. Hull, Journal of Chemical Society, 1951, "A New Synthesis of 4:6–Dihydroxypyrimidines".

*Primary Examiner*—John M. Ford
*Attorney, Agent, or Firm*—Oblon, Spivak, McClelland, Maier & Neustadt, P.C.

[57] ABSTRACT

The invention relates to a process for the preparation of 4,6-dihydroxypyrimidine by reacting malonate with formamide and an alkali metal alkoxide at elevated temperature. In this process, the malonate alone or simultaneously with all or some of the formamide is added in portions or continuously to the alkali metal alkoxide initially introduced as a solution or suspension in an alcohol alone or together with all, or the remainder, of the formamide.

16 Claims, No Drawings

PROCESS FOR THE PREPARATION OF 4, 6-DIHYDROXYPYRIMIDINE

BACKGROUND OF THE INVENTION

1. Field of the Invention

The invention relates to an improved process for the preparation of 4,6-dihydroxypyrimidine (DHP), also termed 1H-pyrimidine-4,6-dione in its tautomeric form, from malonic esters, formamide and alkoxides.

2. Discussion of the Background

DHP is a valuable intermediate for syntheses of active ingredients. Thus, 4,6-dihydroxypyrimidine can be used to prepare the corresponding dichloropyrimidine which, in turn, may be processed to give novel, highly-active fungicides (EP-A1 Nos. 0 382 375, 0 393 861, 0 468 684 and 0 468 695).

In the process for the preparation of DHP as described by R. Hull, J. Chem. Soc., 1951, 2214, malonodiamide and a solution of sodium methoxide in ethanol are combined at room temperature. Ethyl formate is added, and the mixture is then refluxed for 2 hours. Sodium methoxide and ethyl formate are employed in amounts of 1.5 and 2 moles respectively, per mole of malonodiamide. The salts which have precipitated are separated off and dissolved in water, and DHP is precipitated from the solution by adding acid and then separated off. The DHP yield is approximately 40% of theory. These results were confirmed by C. Hennart et al., Bull. Soc. Chim., 1959, 741, but these workers only employed 1 mole of ethyl formate and achieved a crude yield of DHP of 44% of theory.

D. J. Brown, J. Chem. Soc., 1956 reported a modification of Hull's synthesis by replacing the ethyl formate with 1.6 moles of formamide, thus increasing the yield to approximately 52% of theory.

The DHP yield was improved by approximately 30% to a maximum of 81% by A. Sömmer, DE-OS 1 200 308 by reacting malonodiamide with formamide in alcoholic solution with more than 2 moles, advantageously with 3.0 to 3.9 moles, of alkali metal alkoxide. As opposed to Brown, this worker employed formamide in the examples in amounts of just over 2 moles per mole of malonodiamide. The alkali metal alkoxides used were sodium ethoxide in methanol and sodium methoxide in ethanol. In the latter case, the methanol was distilled off from the reaction mixture, thus dispensing with filtration of the salts which had precipitated. Ethyl formate instead of formamide yielded, together with sodium ethoxide, DHP in a yield of only 61.5%.

The preparation of DHP by the method of A. Sömmer, loc. cit., may be described summarily by the following equation:

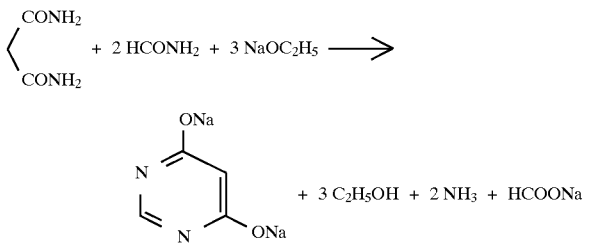

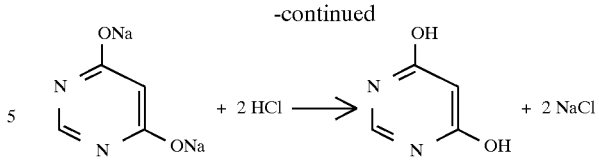

Similar findings are reported by V. A. Zasonov et al. in Khim.-Farm. Zh. Vol. 8, No. 12, 28–31. Using 2 moles of formamide and 3 moles of sodium ethoxide per mole of malonodiamide, they achieved a DHP yield of 83.2%. Zasosov et al. also gave an example for the preparation of the starting material malonodiamide from malonate and ammonia in a yield of 95%. Here, the malonodiamide is isolated before it is reacted to give DHP. Thus, this represents an aggregation of two process steps which are in no way integrated. The DHP yield based on malonate is 79% of theory.

A disadvantage of all processes mentioned so far is that the starting material malonodiamide is not available in commercial amounts. In the processes of Hull, Hennart et al. and Brown, the yields are unsatisfactory. While the processes of A. Sömmer and of V. A. Zasosov et al. give better, albeit not fully satisfactory yields with formamide, they, like the previously mentioned processes, require the starting material malonodiamide, which is prepared from malonate. This means that, stoichiometrically, this and the formamide already introduce 4 moles of nitrogen, of which 1.664 moles are recovered in the DHP in the most advantageous case (V. A. Zasosov et al., yield 83.2%). More than half of the nitrogen is thus lost into the methanol, ethanol or the waste water, in the form of ammonia. Processing methanol or ethanol contaminated with ammonia, for recycling purposes, is difficult and complicated. Moreover, removal of the DHP sodium salt by filtration is a problem since the salts are frequently obtained in ultracrystalline form and are therefore difficult to remove by filtration. Finally, the DHP concentration in the reaction mixture and thus the space-time yield are low. At best, approximately 7 parts by weight of DHP are obtained from 100 parts by weight of reaction mixture.

An improved process for the preparation of DHP is described by Kyowa Hakko in GB-A2-1 092 144. Here, the starting material is an alkyl malonate which is reacted with ammonia or formamide in the presence of an alkali metal catalyst to give malonodiamide, which is then subjected to a condensation with formamide to give DHP. This is therefore a two-step process which, in contrast to Zasosov et al., is carried out in the same reactor without isolating the product from the first step. The alkali metal catalysts used are potassium ethoxide and sodium ethoxide, and not much less than 3 moles of ammonia or formamide are to be employed per mole of malonate. The yields in the 4 examples are calculated as 75 to 90% of theory. However, reproduction of the example with the best yield showed that the sodium salts were very difficult to remove by filtration, and that the actual DHP yield is only 85% of theory.

While the Kyowa Hakko process yields high quantities and starts from the malonic esters, which can be obtained in commercial amounts, it is still not fully satisfactory in its entirety. As shown by the examples, preparation of the malonodiamide in the first step is a problem. Either, reaction times of 48 hours are required, which reduces the space-time yield, as shown in Examples 1 and 2, or there are stirring problems, as described in Example 3. Example 4 uses solid potassium ethoxide, which is hygroscopic and therefore difficult to handle, frequently forms dusts which cause chemical burns and which may undergo spontaneous ignition. Furthermore, to achieve high yields, considerably more than the 3 moles of ammonia or formamide, which are required in the first patent claim, are required per mole of alkyl malonate. In Example 3, 7.7 moles of formamide, and in Example 4 even 10.1 moles of formamide are employed per mole of diethyl malonate. This means that the filtrates obtained after removing the salts by filtration are highly contaminated with ammonia and formamide. In addition, as in the above-described processes, the DHP concentration in the reaction mixture is low, in the best case (Example 3) it is 6 g of DHP per 100 g of reaction mixture. The space-time yields are similarly low.

SUMMARY OF THE INVENTION

It has now been found that 4,6-dihydroxypyrimidine can be prepared advantageously by reacting a malonate with formamide and an alkali metal alkoxide at elevated temperature when the malonate alone or simultaneously with all or some of the formamide is added batchwise or continuously to the alkali metal alkoxide which has been initially introduced as a solution or suspension in an alcohol alone or together with all, or the remainder, of the formamide.

DETAILED DESCRIPTION OF THE PREFERRED EMBODIMENTS

In the event that dimethyl malonate is reacted with formamide and sodium methoxide, the summary reaction equation is as follows:

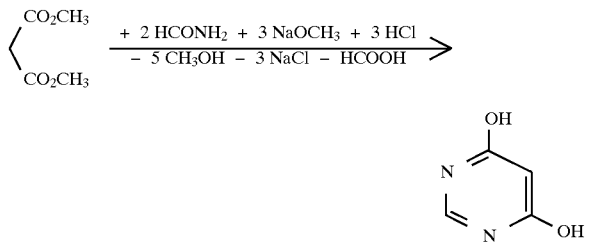

In comparison with the prior-art processes, the process according to the invention has a series of surprising advantages. Instead of malonodiamide, the malonates, which are available in commercial amounts, are used as starting materials, and an integrated process in only one reaction step gives very good yields of the alkali metal salt of the desired DHP, which does not need to be separated from the reaction mixture in order to liberate the DHP by means of acid. In this process, less amine, or amide, nitrogen are utilized for the pyrimidine ring cyclization than in the known processes. Ammonia-free alcohol can be recovered without complicated measures, and waste-water contamination with ammonia or ammonium compounds is kept at a minimum. The DHP concentration in the reaction mixture, and thus the space-time yield, is markedly higher than in the known processes.

The malonates used as starting materials are known, generally inexpensive substances and are generally available in commercial amounts. Non-limiting examples include dimethyl malonate, diethyl malonate, dipropyl malonate and dibutyl malonate. An especially preferred starting material is dimethyl malonate.

Formamide may be employed in the form of an ultrapure or technical-grade product as it is obtained from the industrial-scale synthesis of methyl formate and ammonia. The formamide is expediently used in amounts of from 2.0 to 2.5, in particular 2.1 to 2.25 moles per mole of malonate. Higher amounts of formamide are easily possible, but contradict the aim of minimizing contamination of the fluids obtained with nitrogen-containing substances. Lower amounts of formamide are possible, but the DHP yield will then drop, since 2 moles of nitrogen compound are required for pyrimidine cyclization.

Preferred alkali metal alkoxides are the potassium alkoxides and, in particular, the sodium alkoxides, which are derived from alkanols having 1 to 4 carbon atoms. They are advantageously employed as solutions or suspensions in the alcohol from which they are derived. Accordingly, alkanols having 1 to 4 carbon atoms are the alcohols preferred for the process. Sodium methoxide, which may be used as an inexpensive, commercially available solution of approximately 30% by weight in methanol, is particularly preferred. However, higher-concentrated solutions or suspensions of sodium methoxide or potassium methoxide may be employed without problems with stirring or uncontrollable solidification of the reaction mixture occurring. The use of other alkoxides, for example of sodium ethoxide and potassium ethoxide which are used in the known preparation processes, are also easily possible, but this is not preferred due to the higher price. The amount of the alcohol initially introduced together with the alkali metal alkoxide (or the concentration of the dissolved, or dissolved and suspended, alkali metal alkoxide) determines the DHP alkali metal salt content of the reaction mixture and thus the space-time yield. It is an advantage of the process according to the invention that highly concentrated alkali metal alkoxide solutions or suspensions may be employed. Thus, when using approximately 40% by weight of sodium methoxide in methanol, DHP is obtained after acidification in a yield of 14.5 g/100 g of reaction mixture.

The process according to the invention may be carried out by adding the malonate alone or simultaneously with all or some of the formamide batchwise or continuously to the alkali metal alkoxide which has been initially introduced as a solution or suspension in an alcohol and, if appropriate, all, or the remainder, of the formamide. It is an essential characteristic of the invention that the malonate, either in small amounts or advantageously continuously, is added to the alkali metal alkoxide which has initially been introduced. In contrast, it is irrelevant whether the formamide is initially introduced together with the alkali metal alkoxide or else added to the latter. The formamide may therefore be divided in any ratio to initial reaction mixture and run-in reaction mixture, if appropriate. If the malonate, simultaneously with all or some of the formamide, is added to the initially introduced alkali metal alkoxide, then the formamide may be added separately from the malonate or advantageously as a mixture with the latter.

The temperature in the reaction mixture is expediently held in the range of from 30° to 100° C., in particular 50° to 80° C. The reaction is weakly exothermic, so that cooling may be necessary once addition of malonate has started. Depending on the amounts of substance added, addition of the malonate and, if appropriate the formamide, tin general approximately 15 to 60 minutes. It is advantageous to allow the reaction mixture to post-react for some time after the addition has ended, for example for 30 minutes to 2 hours, at a temperature toward the top of the range mentioned, for example 90° to 100° C.

Reaction and post-reaction are expediently carried out at the pressure which is established at the temperature in question, i.e., in general 1 to 5 bar.

The cooled reaction mixture is treated with water, and the free DHP is liberated from its alkali metal salt by adding an acid, expediently a mineral acid such as sulfuric acid, phosphoric acid and, in particular hydrochloric acid. It is also possible, as described in DE-OS 1 200 308, to evaporate the alcohol out of the alcoholic reaction mixture until a dry state, for what thinfilm evaporators are used with advantage in technique, to dissolve the remaining salts in water and then to liberate DHP as described above by adding an acid. The precipitated DHP is washed in both cases with water and expediently dried at elevated temperature, such as 50° to 90° C., and under reduced pressure, such as 20 to 200 mbar.

The reaction product is obtained in yields which may exceed 90% of theory.

The examples which follow are intended to further illustrate the invention but not to limit its scope as it is described in the patent claims.

Having generally described this invention, a further understanding can be obtained by reference to certain specific examples which are provided herein for purposes of illustration only and are not intended to be limiting unless otherwise specified.

EXAMPLES

Example 1

8.25 moles of sodium methoxide in the form of a 30% by weight solution in methanol and 5.25 moles of formamide are initially introduced into a 5 L rotary autoclave, equipped with stirrer, and the mixture is heated at 50° C. Then, 2.50 moles of dimethyl malonate are continuously pumped in in the course of 60 minutes, during which process the temperature climbs to 65° C. The mixture is allowed to post-react for one hour at 95° C., the pressure is released, and the autoclave is flushed with nitrogen. Then, the reaction mixture is treated with 1,150 ml of water, and 7.0 moles of 36% strength by weight aqueous hydrochloric acid are added dropwise, the temperature being held at 20° to 25° C. by cooling. The precipitated DHP is filtered off with suction and washed three times with water. After drying at 70°–80° C./20–30 mbar, 235.4 g of DHP are obtained, which corresponds to a yield of 84.0% of theory. Only 1.05 moles of nitrogen of the 5.25 moles which had been employed in the form of formamide are lost, which corresponds to 62.5 g per kg of DHP. In the most advantageous example to date, which was described by V. A. Zasosov et al., 351 g of nitrogen were lost per kg of DHP.

Example 2

8.25 moles of sodium methoxide, dissolved or suspended in methanol (solids content 41.4% by weight) are initially introduced into a 5 L rotary autoclave, equipped with stirrer, and heated at 75° C. Then, a mixture of 2.5 moles of dimethyl malonate and 5.6 moles of formamide are continuously pumped in over the course of 60 minutes, during which process the temperature climbs to 85° C. The reaction mixture is allowed to post-react as described in Example 1 and worked up analogously by adding 900 ml of water and 7.0 moles of 36% strength by weight aqueous hydrochloric acid. The yield is 246.6 g, which corresponds to 88.0% of theory. The nitrogen loss per kg of DHP amounts to 68.2 g.

Example 3

8.25 moles of a 41.4% suspension of sodium methoxide in methanol and 5.60 moles of formamide are initially introduced into a 5 L rotary autoclave, equipped with stirrer, and heated at 60° C. Then, 2.50 moles of dimethyl malonate are pumped in over the course of 60 minutes, during which process the temperature slowly climbs to 65° C. The reaction mixture is allowed to post-react as described in Example 1 and worked up analogously using 900 ml of water and 7.0 moles of 36% strength aqueous hydrochloric acid. The yield amounts to 254.7 g, which corresponds to 90.9% of theory. 58 g of nitrogen were lost per kg of DHP.

Obviously, numerous modifications and variations of the present invention are possible in light of the above teachings. It is therefore to be understood that within the scope of the appended claims, the invention may be practiced otherwise than as specifically described herein.

This application is based on German patent applications DE 196,26,747.1 and 196,40,756.7 filed in the German Patent Office on Jul. 3, 1996 and Oct. 2, 1996, the entire contents of which are hereby incorporated by reference.

What is claimed as new and desired to be secured by Letters Patent of the United States is:

1. A process comprising: adding a malonate to an alkali metal alkoxide, in the presence of a formamide, to form 4,6-dihydroxypyrimidine.

2. The process of claim 1, wherein said malonate is added to said alkali metal alkoxide simultaneously with said formamide.

3. The process of claim 1, wherein said malonate is added to said alkali metal alkoxide and said formamide.

4. The process of claim 1, wherein said alkali metal alkoxide is a solution in said alcohol.

5. The process of claim 1, wherein said alkali metal alkoxide is a suspension in said alcohol.

6. The process of claim 1, wherein said malonate is added in portions to said alkali metal alkoxide.

7. The process of claim 1, wherein said malonate is added continuously to said alkali metal alkoxide.

8. The process of claim 1, wherein the temperature in the reaction mixture is 30° to 100° C., while said malonate is added.

9. The process of claim 1, wherein the temperature in the reaction mixture is 50° to 80° C., while said malonate is added.

10. The process of claim 1, wherein 2.0 to 2.5 moles of formamide and 3.0 to 4.0, moles of alkali metal alkoxide are used per mole of malonate.

11. The process of claim 1, wherein 2.1 to 2.25, moles of formamide and 3.0 to 3.5, moles of alkali metal alkoxide are used per mole of malonate.

12. The process of claim 1, wherein said alkali metal alkoxide is selected from the group consisting of sodium methoxide, potassium methoxide and a mixture thereof, in the form of a suspension or solution in methanol.

13. The process of claim 1, wherein said malonate is dimethyl malonate, diethyl malonate or a mixture thereof.

14. The process of claim 1, wherein said reaction is carried out under the pressure which is established at the reaction temperature in question.

15. The process of claim 1, further comprising obtaining said reaction product by treating said reaction mixture with water and precipitating said reaction product by adding acid.

16. The process of claim 1, wherein said alcohol is distilled out of said reaction mixture by means of a thin film evaporator, the remaining salts are dissolved in water and 4,6-dihydroxypyrimidine is precipitated by adding an acid.

* * * * *